United States Patent
McPeak et al.

(10) Patent No.: US 10,612,070 B2
(45) Date of Patent: Apr. 7, 2020

(54) FLUID HOLDING AND DISPENSING MICRO-FEATURE

(71) Applicant: Ativa Medical Corporation, St. Paul, MN (US)

(72) Inventors: Daniel R. McPeak, Minneapolis, MN (US); Ka Man Lee, Minneapolis, MN (US); Eric R. Peltola, Minneapolis, MN (US)

(73) Assignee: Ativa Medical Corporation, St. Paul, MN (US)

( * ) Notice: Subject to any disclaimer, the term of this patent is extended or adjusted under 35 U.S.C. 154(b) by 0 days.

(21) Appl. No.: 15/397,349

(22) Filed: Jan. 3, 2017

(65) Prior Publication Data

US 2017/0114386 A1 Apr. 27, 2017

Related U.S. Application Data

(62) Division of application No. 14/837,524, filed on Aug. 27, 2015, now abandoned.

(51) Int. Cl.
*C12Q 1/24* (2006.01)
*G01N 33/80* (2006.01)
(Continued)

(52) U.S. Cl.
CPC .......... *C12Q 1/24* (2013.01); *B01L 3/502707* (2013.01); *B01L 3/502753* (2013.01);
(Continued)

(58) Field of Classification Search
CPC combination set(s) only.
See application file for complete search history.

(56) References Cited

U.S. PATENT DOCUMENTS

| 3,521,715 A | 7/1970 | Krutein |
| 4,038,875 A | 8/1977 | Walkotten |

(Continued)

FOREIGN PATENT DOCUMENTS

| WO | WO 2007076549 | 7/2007 |
| WO | WO 2014149310 | 9/2014 |
| WO | WO 2015009284 | 1/2015 |

OTHER PUBLICATIONS

Haandel and van der Lubbe, "Handbook Biological Waste Water Treatment: Design and optimisation of activated sludge systems," Chapt. 6, pp. 248-255, 2007.

(Continued)

*Primary Examiner* — Brian R Gordon
(74) *Attorney, Agent, or Firm* — Fish & Richardson P.C.

(57) ABSTRACT

Apparatus, system and method for dispensing a particle-laden fluid from a fluid holding and dispensing micro-feature. In some implementations, the apparatus includes: a chamber having one or more surfaces that define a volume to receive fluid containing particulate matter, and an outlet port to dispense at least a portion of the fluid from the chamber. The outlet port may have a normal vector that, when the apparatus is positioned to dispense the fluid, is substantially perpendicular to gravity. The apparatus may be used to measure a number of individual particles from the fluid that flow through the outlet port over a period of them, measure a total volume of the fluid dispensed through the outlet port over the period of time, and calculate a concentration of the particulate matter within the chamber. In some implementations, the particle-laden fluid may be whole blood.

11 Claims, 6 Drawing Sheets

(51) Int. Cl.
*G01N 1/40* (2006.01)
*B01L 3/00* (2006.01)
(52) U.S. Cl.
CPC .......... *G01N 1/4077* (2013.01); *G01N 33/80* (2013.01); *B01L 2200/0652* (2013.01); *B01L 2200/10* (2013.01); *B01L 2300/0816* (2013.01); *B01L 2300/0858* (2013.01); *B01L 2300/0864* (2013.01); *B01L 2300/16* (2013.01); *B01L 2400/0457* (2013.01)

(56) References Cited

U.S. PATENT DOCUMENTS

| | | | |
|---|---|---|---|
| 4,040,959 | A | 8/1977 | Irwin et al. |
| 6,136,272 | A | 10/2000 | Weigl |
| 6,159,739 | A | 12/2000 | Weigl |
| 6,186,409 | B1 | 2/2001 | Srinath et al. |
| 6,382,228 | B1 | 5/2002 | Cabuz et al. |
| 6,454,945 | B1 | 9/2002 | Weigl |
| 6,488,894 | B1* | 12/2002 | Miethe ............... B01F 13/0071 137/197 |
| 6,537,501 | B1 | 3/2003 | Holl et al. |
| 6,541,213 | B1 | 4/2003 | Weigl |
| 6,549,275 | B1 | 4/2003 | Cabuz et al. |
| 6,557,427 | B2 | 5/2003 | Weigl et al. |
| 6,674,525 | B2 | 1/2004 | Bardell et al. |
| 6,706,245 | B2 | 3/2004 | Neal |
| 7,061,595 | B2 | 6/2006 | Cabuz et al. |
| 7,229,594 | B2 | 6/2007 | Renaud |
| 7,242,474 | B2 | 7/2007 | Cox et al. |
| 7,277,166 | B2 | 10/2007 | Padmanabhan et al. |
| 7,420,659 | B1 | 9/2008 | Cabuz et al. |
| 7,517,498 | B2 | 4/2009 | Fredrick |
| 7,527,109 | B2 | 5/2009 | Barker |
| 7,641,856 | B2 | 1/2010 | Padmanabhan et al. |
| 8,034,296 | B2 | 10/2011 | Cox et al. |
| 8,071,051 | B2 | 12/2011 | Padmanabhan et al. |
| 8,097,225 | B2 | 1/2012 | Padmanabhan et al. |
| 8,323,564 | B2 | 12/2012 | Padmanabhan et al. |
| 8,329,118 | B2 | 12/2012 | Padmanabhan et al. |
| 8,361,410 | B2 | 1/2013 | Padmanabhan et al. |
| 8,372,354 | B2 | 2/2013 | Killen |
| 8,383,043 | B2 | 2/2013 | Padmanabhan et al. |
| 8,741,233 | B2 | 6/2014 | Bardell et al. |
| 2004/0043506 | A1 | 3/2004 | Haussecker et al. |
| 2006/0246575 | A1 | 11/2006 | Lancaster et al. |
| 2006/0263888 | A1 | 11/2006 | Fritz et al. |
| 2009/0101575 | A1* | 4/2009 | Alburty ............... G01N 1/4077 210/636 |
| 2010/0104479 | A1 | 4/2010 | Alex et al. |
| 2011/0275111 | A1 | 11/2011 | Pettigrew et al. |
| 2013/0095007 | A1* | 4/2013 | Haubert ............ B01L 3/50215 422/533 |
| 2013/0203157 | A1 | 8/2013 | Cheung et al. |
| 2014/0008210 | A1 | 1/2014 | Antonio et al. |
| 2014/0234828 | A1 | 8/2014 | Walter |
| 2014/0315238 | A1 | 10/2014 | Farrell et al. |
| 2015/0165346 | A1 | 6/2015 | Michael et al. |
| 2017/0059590 | A1 | 3/2017 | McPeak et al. |
| 2017/0074759 | A1* | 3/2017 | Campton ............ H01L 24/03 |

OTHER PUBLICATIONS

International Preliminary Report on Patentability in Internation Application No. PCT/US2016/049324.
International Search Report and Written Opinion for International Application No. PCT/US2016/049324, dated Nov. 24, 2016, 11 pages.
Szeto et al., "Microfluidic squeezing for intracellular antigen loading in polyclonal B-cells as cellular vaccines," *Sci Rep.* 5:10276, 13 pages, May 22, 2015.
Yflow, "Coaxial Electrospinning Machines: R&D Microencapsulation," [retrieved Sep. 11, 2015]. Retrieved from the Internet: <URL: http://www.yflow.com/technology/coaxial_coflowing/>, 4 pages.

* cited by examiner

FLUID HOLDING AND DISPENSING MICRO-FEATURE

CROSS-REFERENCE TO RELATED APPLICATION

This application is a divisional application of and claims priority to U.S. application Ser. No. 14/837,524, filed on Aug. 27, 2015, the entire contents of which are hereby incorporated by reference.

TECHNICAL FIELD

The present specification relates to fluid dispensing features for use with fluidic devices, such as microfluidic devices that perform cell counting techniques.

BACKGROUND

When dispensing fluids containing particulate matter, such as whole blood containing blood cells (example particulate matter), sedimentation can occur over time as the particulate matter settles out. Such sedimentation can result in regions of the fluid becoming inhomogeneous with different concentrations of the particulate matter. Techniques to agitate fluids with particulate matter have been used to avoid the effects of sedimentation and to ensure that fluids are dispensed with the same or similar concentrations of particulate matter. A variety of agitation techniques have been used, such as shaking a container holding a fluid with particulate matter and mixing/stirring such a fluid within a container.

Fluid dispensing techniques have been used in a variety of applications, such as cell counting techniques that allow for quantification of particulate matter within liquid media, such as blood, plasma, or lymph. In clinical practice, cell counting has been used to provide information related to physiological conditions that indicate, or result from, the presence of infectious diseases. For example, complete blood count (CBC) can be used for medical diagnosis and treatment of various diseases.

SUMMARY

This document generally describes fluid holding and dispensing micro-features that can be used to dispense fluids containing particulate matter over time with near uniform concentrations of particulate matter without using techniques to agitate the fluid and to avoid the effects of sedimentation. Such fluid holding and dispensing micro-features can allow for the measurement of particulate concentration within a particle-laden fluid based on the volumetric displacement of the fluid through the micro-feature.

For example, such a micro-feature can include a chamber that is oriented perpendicular to an outlet port such that the particle transport rate out of the chamber is proportional to the volumetric flow rate of a particle-laden fluid from the chamber and the proportionality constant represents the particulate concentration within the fluid. The outlet port can be positioned on a vertical sidewall of the chamber such that the fluid exiting the chamber additionally follows a constant particle flow rate that is in agreement with the concentration of the particulate matter within the fluid. Accordingly, the micro-feature can be used to inferentially determine the particulate concentration of the fluid within the chamber based on measuring the bulk volumetric flow rate of dispensed fluid through the outlet port.

Implementations may include one or more of the following features. For example, a apparatus for dispensing fluid, the apparatus including: a chamber having one or more surfaces that define a volume to receive fluid containing particulate matter, where the fluid within the chamber includes, at least, a top region, a middle region, and a bottom region that, after at least a threshold time period has elapsed since the fluid is received into the chamber, contain different concentrations of the particulate matter, with (i) the top region containing less than or equal to a first threshold concentration of the particulate matter, (ii) the middle region containing between the first threshold concentration of the particulate matter and a second threshold concentration of the particulate matter, and (iii) the bottom region containing greater than or equal to the second threshold concentration of the particulate matter, where the first threshold concentration is less than the second threshold concentration; and an outlet port to dispense at least a portion of the fluid from the chamber in concentrations that are between the first threshold concentration and the second concentration, the outlet port (i) located at a position in the chamber that corresponds to the middle region and (ii) having a normal vector that, when the apparatus is positioned to dispense the fluid, is substantially perpendicular to gravity.

One or more implementations of the apparatus may include the following optional features. For example, in some implementations, the fluid containing particulate matter includes whole blood and the particulate matter includes blood cells.

In some implementations, after at least the threshold time period has elapsed since the whole blood is received into the chamber, the: the top region contains a plasma supernatant of the whole blood; the middle region contains pristine blood with blood cell concentrations that are within a threshold range of a blood cell concentration of the whole blood when it is initially received into the chamber; and the bottom layer contains a packed cell layer that results from sedimentation over the threshold time period.

In some implementations, the apparatus further includes one or more inlet ports for the chamber that are configured to receive another fluid that, once received into the chamber, will force the fluid in the middle region of the chamber to be dispensed through the outlet port in the direction that is substantially perpendicular to gravity.

In some implementations, at least one of the one or more inlet ports is connected to the top region of the chamber, and the other fluid received through the at least one of the one or more inlet ports is less dense than the fluid containing particulate matter.

In some implementations, at least one of the one or more inlet ports is connected to bottom region of the chamber, and the other fluid received through the at least one of the one or more inlet ports is more dense than the fluid containing particulate matter.

In some implementations, the one or more inlet ports include, at least, (i) a first inlet port that is connected to the top region of the chamber and (ii) a second inlet port that is connected to the bottom region of the chamber, the other fluid includes a first fluid received through the first inlet port that is less dense than the fluid containing particulate matter, and the other fluid additionally includes a second fluid received through the second inlet port that is more dense than the fluid containing particulate matter.

In some implementations, the middle region decreases in size and the top and bottom regions increase in size over time as sedimentation of the particulate matter in the fluid occurs.

In some implementations, the outlet port is positioned along at least one vertical sidewall of the chamber on a plane that corresponds to an average point of convergence between the top region and the bottom region across a range of fluid samples containing the particulate matter.

In some implementations, the apparatus further includes an microfluidic cartridge that includes one or more microfluidic circuits through which the fluid dispensed from the chamber via the outlet port is analyzed, and the microfluidic cartridge is configured to be inserted into an analyzer device that is configured and programmed to (i) control the fluid being dispensed from the chamber and (ii) analyze the fluid dispensed from the chamber.

In some implementations, the microfluidic cartridge is disposable.

In some implementations, the apparatus further includes an analyzer device that is configured and programmed to (i) control the fluid being dispensed from the chamber and (ii) analyze the fluid dispensed from the chamber.

In some implementations, the apparatus further includes a second outlet port to dispense at least a portion of the fluid from the chamber in concentrations that are between the first threshold concentration and the second concentration, the second outlet port (i) located at a position in the chamber that corresponds to the middle region and (ii) having a normal vector that, when the apparatus is positioned to dispense the fluid, is substantially perpendicular to gravity.

In some implementations, a method may include: injecting a fluid containing particulate matter into a fluidic circuit including at least (i) a chamber having one or more surfaces that define a volume to receive the fluid containing particulate matter, where the fluid within the chamber includes, at least, a top region, a middle region, and a bottom region that, after at least a threshold time period has elapsed since the fluid is received into the chamber, contain different concentrations of the particulate matter, and (ii) an outlet port located at a position in the chamber that corresponds to the middle region; dispensing a portion of the fluid containing particulate matter from the middle region of the chamber via the outlet port such that the fluid containing particulate matter flows from the chamber and into the outlet port in a direction that is substantially perpendicular to gravity; and stopping, while the top and bottom regions of the chamber still include another portion of the fluid containing particulate matter, the dispensing of the fluid containing particulate matter based on one or more criteria being met.

One or more implementations of the method may include the following optional features. For example, in some implementations, the one or more criteria being met include a particular period of time having elapsed since the fluid containing particulate matter was injected into the fluidic circuit having elapsed, and the particular period of time corresponds to the fluidic circuit.

In some implementations, the method further includes: measuring, by an analyzer device, a number of individual particles from the fluid that flow through the outlet port over a period of time; measuring, by the analyzer device, a total volume of the fluid dispensed through the outlet port over the period of time; calculating, by the analyzer device, a remaining concentration of the particulate matter within the chamber based at least on (i) the number of individual particles measured as flowing through the outlet port, and (ii) the measured total volume of the fluid dispensed over the period of time; and determining, by the analyzer device, whether the remaining concentration of the particulate matter in the fluid is greater than a threshold concentration for dispensing through the outlet port, where the one or more criteria being met include the remaining concentration of the particulate matter being greater than the threshold concentration.

In some implementations, the fluid containing particulate matter includes whole blood, and determining the remaining concentration of the particulate matter within chamber includes determining a red blood cell concentration within the whole blood in the chamber.

In some implementations, the number of individual particles is measured for fluid contained in the middle region of the fluid in the chamber having a threshold concentration of the particulate matter that is (i) greater than a first threshold concentration of the particulate matter within the top region of the chamber, and (ii) less than a second threshold concentration of the particulate matter within the bottom region.

In some implementations, the number of individual particles is measured using one or more optical detectors that are part of or in communication with the analyzer device.

In some implementations, the dispensing includes injecting another fluid into the chamber after injecting the fluid containing particulate matter into the fluidic circuit, where the other fluid forces individual particles from among the particulate matter of the fluid to be dispensed through the outlet port.

In some implementations, injecting the another fluid into the chamber includes injecting the other fluid into at least one of one or more inlet ports that is connected to the top region of the chamber, where the other fluid is less dense than the fluid containing particulate matter.

In some implementations, injecting the reagent fluid into the chamber includes injecting the other fluid into at least one of one or more inlet ports that is connected to the bottom region of the chamber, where the other fluid is more dense than the fluid containing particulate matter.

In some implementations, the fluid containing particulate matter includes whole blood, and after at least the threshold time period has elapsed since the whole blood is received into the chamber: the top region contains a plasma supernatant of the whole blood, the middle region contains pristine blood with blood cell concentrations that are within a threshold range of a blood cell concentration of the whole blood when it is initially received into the chamber, and the bottom layer contains a packed cell layer that results from sedimentation over the threshold time period.

In some implementations, the method further includes dispensing a portion of the fluid containing particulate matter from the middle region of the chamber via a second outlet port such that the fluid containing particulate matter flows from the chamber and into the outlet port in a direction that is substantially perpendicular to gravity.

In some implementations, a system for dispensing fluid includes: a fluidic circuit configured to receive a fluid containing particulate matter; a chamber having one or more surfaces that define a volume to receive the fluid containing particulate matter from the fluidic circuit, where the fluid within the chamber includes, at least, a top region, a middle region, and a bottom region that, after at least a threshold time period has elapsed since the fluid is received into the chamber, contain different concentrations of the particulate matter, with (i) the top region containing less than or equal to a first threshold concentration of the particulate matter, (ii) the middle region containing between the first threshold concentration of the particulate matter and a second threshold concentration of the particulate matter, and (iii) the bottom region containing greater than or equal to the second threshold concentration of the particulate matter, where the first threshold concentration is less than the second threshold concentration; and a outlet port, positioned along at least one vertical wall of the chamber, configured to receive a portion of the fluid from the chamber in concentrations that are between the first threshold concentration and the second concentration, the outlet port (i) located at a position in the chamber that corresponds to the middle region and (ii) having a normal vector that, when the apparatus is positioned to dispense the fluid, is substantially perpendicular to gravity.

In some implementations, the system further includes an analyzer device that is configured and programmed to (i) control the fluid being dispensed from the chamber and (ii) analyze the fluid dispensed from the chamber.

In some implementations, the analyzer device includes the fluidic circuit, the chamber, and the outlet port.

In some implementations, the system further includes a cartridge that is configured to be inserted into the analyzer device, where the cartridge includes the fluidic circuit, the chamber, and the outlet port.

In some implementations, the system further includes a second outlet port, positioned along at least one vertical wall of the chamber, configured to receive a portion of the fluid from the chamber in concentrations that are between the first threshold concentration and the second concentration, the second outlet port (i) located at a position in the chamber that corresponds to the middle region and (ii) having a normal vector that, when the apparatus is positioned to dispense the fluid, is substantially perpendicular to gravity.

The details of one or more implementations are set forth in the accompanying drawings and the description below. Certain implementations can provide any of a variety of advantages. For example, the effects of sedimentation can be negated without relying on techniques to agitate a fluid containing particulate matter which, in some contexts, may not be possible. For instance, a microfluidic circuit that includes a chamber or microfluidic channel that holds and dispenses fluid (e.g., whole blood) into the circuit may not be readily agitated, such as through shaking the circuit or mixing/stirring the fluid. Micro-features described in this document can be used to allow for such a fluid to be dispensed with a near constant particle flow rate in spite of ongoing sedimentation.

Other potential features and advantages will become apparent from the description, the drawings, and the claims.

Other implementations of these aspects include corresponding systems, apparatus and computer programs, configured to perform the actions of the methods, encoded on computer storage devices.

BRIEF DESCRIPTION OF THE DRAWINGS

In the drawings, like reference numbers represent corresponding parts throughout.

DETAILED DESCRIPTION

Dispensing fluids containing particulates and performing operations using dispensed fluids, such as cell counting, particularly within micro-environments, can pose various challenges based on, for example, properties of fluids containing particulate matter and/or complexities in quantifying particulate matter. For example, coagulating properties of whole blood (example fluid containing particulate matter) can cause it to become inhomogeneous while flowing through microfluidic passages. In another example, sedimentation within a chamber or channel holding whole blood can cause concentrations of blood cells to stratify as time passes. These example factors can cause errors in analytical operations performed on the fluids, such as in cell counting techniques due to non-uniform distribution of cells throughout the microfluidic chambers where measurements can be taken.

This document describes apparatuses, systems, and techniques for holding and dispensing micro-features to mitigate the tendency for particle-laden fluids, for example, whole blood, to become inhomogeneous under low-shear flow conditions. Such apparatuses, systems, and techniques can be implemented in any of a variety of contexts, such as in disposable cartridges that can be used by analyzer devices to analyze fluids injected into the disposable cartridges, reusable cartridges that can be used by analyzer devices to analyze fluids injected into the reusable cartridges, analyzer devices that can include such micro-features, and/or other appropriate devices/apparatuses/systems.

Figure 1:
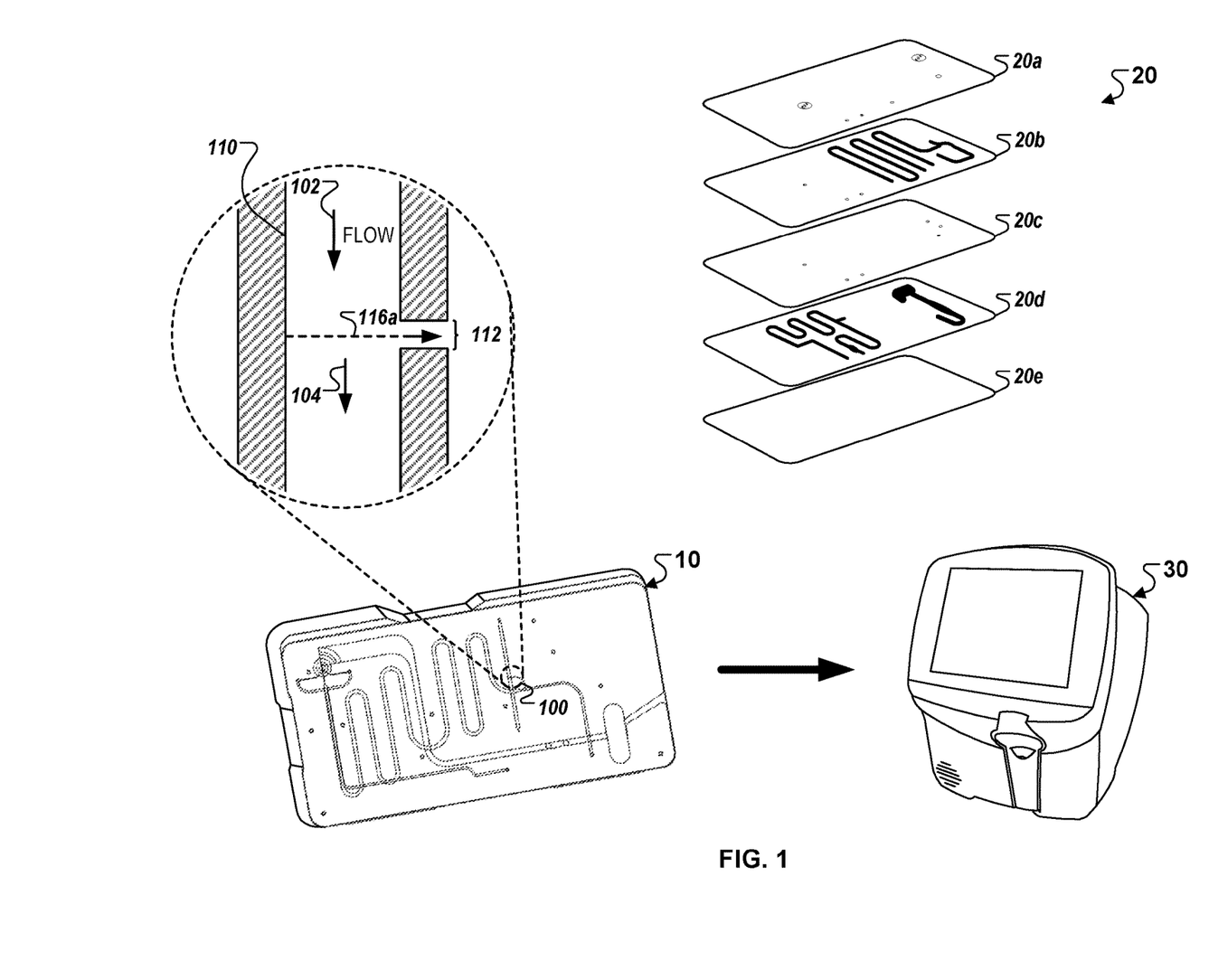
FIG. 1 illustrates components of an exemplary system.

FIG. 1 illustrates components of an exemplary system that uses an example micro-feature to dispense fluid containing particulate matter. The example system that is depicted includes a cartridge 10 that can receive a fluid, such as whole blood, and that can be inserted into an analyzer device 30 for analysis. The analyzer device 30 can perform various tests on the fluid contained in the cartridge 10 by circulating the fluid within the cartridge 10 in particular ways using fluidic circuits and a dispensing micro-feature 100 that are contained within the cartridge 10. The example micro-feature 100 can include a chamber 110 and an outlet port 112 that permit near uniform fluids containing particular matter to be dispensed into the fluidic circuits and analyzed by the analyzer device 30. The cartridge 10, which can be disposable (e.g., intended for a single use) and/or reusable (e.g., able to be used multiple times without performance degradation), can be, for example, fabricated by attaching one or more laminated sheets 20 containing the channels of the fluidic circuit.

As described in more detail below, the example fluid holding and dispensing micro-feature can include a chamber 110 and an outlet port 112 that is arranged perpendicularly on an outlet plane 116a such that when fluid is inserted into the chamber 110, a portion of the fluid maintains a uniform cell distribution within a particular region of the chamber 110 where the outlet port can be placed. A portion of the fluid within the chamber 110 may then be dispensed through the outlet port 112 in a controlled manner, generating a near constant bulk volumetric flow rate of particulate matter through the outlet port 112. The outlet port 112 can define an opening in a sidewall of the chamber 110 through which fluid in the chamber is dispensed from the chamber 110, for example, into one or more fluidic circuits. The particle dispense rate through the outlet port 112 can be measured to calculate a concentration of the particulate matter within the fluid passing through the chamber 110. In some embodiments, the fluid that is inserted into and dispensed form the chamber 110 can be whole blood. Other particle-laden fluids may also be used with the example micro-feature 100.

The cartridge 10 can be a low-cost apparatus that that can include different types of fluidic circuits that are formed within the cartridge 10, such as through the multiple sheets 20, for analyzing fluid samples during testing procedures. The cartridge 10 can be fabricated using any of a variety of appropriate manufacturing techniques, such as injection molding, embossing, laser ablation, machining, etching, lamination, and/or various combinations of such techniques. The cartridge 10 can also be manufactured using various materials such as metal, metal alloys, silicon, plastics, polymers, and/or various combinations of such materials.

Fluidic circuits within the cartridge 10 can include various regions to receive, process, and output fluid samples during testing procedures. For instance, the fluidic circuits can include a sample inlet for inserting a fluid sample to be analyzed, multiple reagent inlets involved in the testing procedure, a reaction-sustaining channel where a particular reaction is performed to generate results of the testing procedure, and a circuit outlet where the fluid sample and/or other waste products are dispensed from the cartridge 10. Other fluidic circuits and/or features are also possible.

Fluid may be collected and introduced into the cartridge 10 and/or the micro-feature 100 by any suitable technique. For example, a blood sample may be collected from a patient by a finger prick directly on the cartridge 10 such that the blood sample is collected and directly introduced to the cartridge 10 and/or the micro-feature 100. In other exemplary embodiments, blood may be collected by a finger prick and subsequently introduced to the cartridge 10 and/or the micro-feature 100.

In some implementations, the cartridge 10 can be fabricated using a single laminated sheet. In other implementations, the cartridge 10 can be fabricated using a combination of multiple laminated sheets 20 that can be manufactured separately and/or composed of different materials. For example, the multiple laminated sheets 20 can have different structural properties such as, differing levels of rigidity, elasticity, and/or hardness, to improve the overall strength and durability of the cartridge 10. In another example, the multiple laminated sheets 20 can include individual sheets with different flexibilities such that the flexible layers can be used to form a valve structure within the cartridge 10. In other examples, coating materials can be used for certain layers of laminated sheets that include fluidic circuits that are used to perform reactions with reagents and/or fluid samples.

As shown in FIG. 1, in one example implementation, the multiple laminated sheets 20 includes layers 20a-e, to form the single cartridge 10. In such an implementation, the top and bottom layers, 20a and 20e, respectively, can be made from acrylic to increase the overall durability of the cartridge 10. The intermediate layers 20b-d can be made from mylar and can include adhesive tacking to bond the multiple laminated sheets 20. The layers 20b and 20d can include fluidic circuits that can be used alternatively and/or in combination to perform sample analysis. For example, the layer 20b can be used to run a fluid sample and layer 20d can be used to run reagent fluid. In another example, the layer 20a can be used to run a sample, and the layer 20b can be used to collect waste products generated from reactions taking place within the fluidic circuit. Other uses, configurations, compositions, properties, and/or arrangements of the layers 20a-e are also possible.

The analyzer device 30 can be a multi-platform point-of-care device capable of performing multiple clinical diagnostic tests using small fluid sample volumes that are injected into the cartridge 10. The analyzer device 30 can be configured to operate with different types disposable cartridges 10 that are adapted to implement various different detection techniques, such as flow cytometry, electrochemistry, colorimetric analysis, and/or imaging of whole blood. For example, in some instances, the analyzer device 30 can be used to perform electrochemical analyses of analytes within a whole blood sample for a basic metabolic panel (BMP). In other instances, the analyzer device 30 can be used to perform flow cytometry assays for detection of particular types of white blood cells such as CD3, CD4, CD8, and C-reactive proteins (CRP), bead-based assays, reflectance spectroscopy for comprehensive metabolic panel (CMP), and/or imaging for determining a erythrocyte sedimentation rate (ESR).

The analyzer device 30 can also include various subsystems that allows the analyzer device 30 to be used as a single-format testing apparatus for performing commonly-occurring blood tests. For example, the analyzer device 30 may include cellular and/or protein analysis subsystems for performing optical/fluorescence flow cytometry and imaging, electrochemical subsystems, and/or photochemical subsystems for performing reflectance/absorption calorimetry and chemiluminescence. In such examples, the subsystems can be physically and/or logically co-housed within a single apparatus such that the analyzer device 30 can be used with different types of cartridges 10 that are specifically designed for various testing procedures. The example micro-feature 100 can be incorporated into various different types of cartridge designs and can be used to dispense fluids to perform various tests by the analyzer device 30.

The analyzer device 30 can also include a user interface, including a display and input features (e.g., touchscreen, keypad, buttons), that allows healthcare professionals or other users to select experimental tests to be performed by the analyzer device 30, to adjust testing parameters, to insert fluid sample information, to view prior or current test results, and/or to transmit the test results over a network. For example, the analyzer device 30 can be used to perform diagnostic tests in low-resource environments, to provide results to onsite medical professional, and to transmit the generated results to a centralized healthcare infrastructure, such as a hospital and/or an electronic medical record system.

For example, the system depicted in FIG. 1 can be used perform cell counting of particular analytes, such as red blood cells, white blood cells, and/or hemoglobin platelets within a whole blood sample. For instance, a whole blood sample can be injected into cartridge 10 and received in the chamber 110 as part of the fluid holding and dispensing micro-feature 100. As the whole blood sample is dispensed from the chamber 110 through the outlet port 112, the analyzer device 30 can be used to detect cells that are dispensed through the outlet port 112 and to perform various tests on the dispensed cells. Other uses of the micro-feature 100 and the cartridge 10 by the analyzer device 30 are also possible.

Cartridge 10, analyzer device 30, and/or micro-feature 100 thus provide a compact, efficient and easy to use system that may be readily implemented at a point-of-care location. Such a system may in some embodiments allow a blood sample to be collected, introduced to micro-feature 100, and analyzed, with results available contemporaneously and in an efficient manner. Accordingly, an exemplary system minimizes additional processing steps and associated costs that may otherwise result when a sample must be sent to a dedicated processing laboratory or facility according to traditional analysis techniques. Further, an exemplary system may provide immediate results, increasing the availability of information for a doctor to diagnose and treat a patient, and thus improve overall quality of care.

Figure 2:
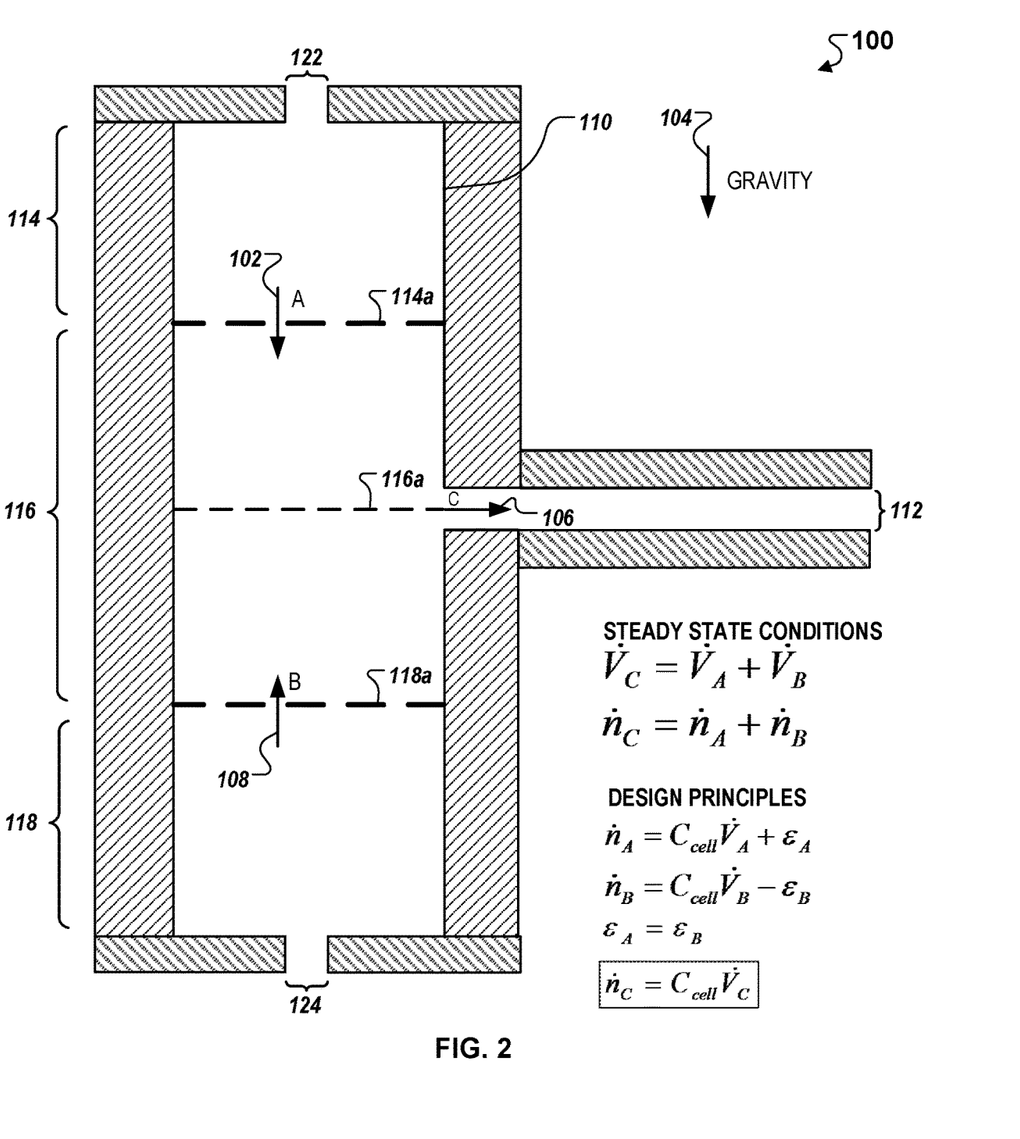
FIG. 2 illustrates design principles of an exemplary fluid holding and dispensing micro-feature.

FIG. 2 depicts a cross-section view of an example fluid holding and dispensing micro-feature 100. As depicted, the example fluid holding and dispensing micro-feature 100 includes a chamber 110 to receive and hold a fluid sample, and an outlet port 112 to dispense the fluid sample from the chamber 110 in a rate-controlled manner. The chamber 110 can act as a sedimentation column such that, after the fluid sample is received by the chamber 110, regions 114, 116, and 118, representing fragmented portions of the fluid sample with varying particulate concentrations within the chamber 110, develop as a result of particle sedimentation from a gravitational force 104. Specifically, particles within the fluid sample are displaced downstream towards the region 118 as time elapses after the fluid is received by the chamber 110.

Implementations of the example fluid holding and dispensing micro-feature 100 may include different inlet ports to receive the sample fluid into the chamber. As depicted, in some implementations, the chamber 110 can be attached to an inlet port 122 that transports the sample fluid into the top region 114. In other implementations, the chamber 110 can alternatively be attached to an inlet port 124 that transports the sample fluid into the bottom region 124. In other implementations, the chamber 110 may also be attached to both the inlet ports 122 and 124.

The example fluid holding and dispensing micro-feature 100 that is designed to observe control-volume principles that conserve physical properties of fluids. For instance, the micro-feature 100 can be designed to conserve energy and mass of the received fluid sample as the fluid sample is displaced through the chamber 110. At steady state, the bulk volumetric flow rate of fluid sample transported into the chamber 110 is equal to the bulk volumetric flow rate of a portion of the fluid sample that is dispensed through the outlet port 112, as shown by equation 1:

$$\dot{V}_C = \dot{V}_A + \dot{V}_B \quad (1)$$

where $\dot{V}_A$ represents the bulk volumetric flow rate of the fluid sample from the top region 114, $\dot{V}_B$ represents the bulk volumetric flow rate of the fluid sample from the bottom region 118, and $\dot{V}_C$ represents the resulting bulk volumetric flow rate of fluid that is dispensed through the outlet port 112.

As the fluid sample is fragmented within the chamber 110 (as a result of sedimentation), the volume of fluid sample within the top region 114, the middle region 116, and the bottom region 118, the sedimentation of particulate matter causes varying distributions of particles within the top region 114, the middle region 116, and the bottom region 118. For instance, the middle region 116 contains volume of fluid sample with a uniform distribution of particulate matter is displaced downstream due to sedimentation. At steady state, the number of individual particles from among the particulate matter of the fluid sample flows through the chamber 110 according to the expression represented by equation 2:

$$\dot{n}_C = \dot{n}_A + \dot{n}_B \quad (2)$$

where $\dot{n}_A$ represents the particle transport rate of fluid sample transported into the chamber 110 from the top region 114, $\dot{n}_B$ represents the particle transport rate of fluid sample transported into the chamber 110 from the bottom region 118, and $\dot{n}_C$ represents the particle transport rate of fluid dispensed through the outlet port 112. Thus, under steady state conditions, the particle transport rate of the fluid dispensed through the outlet port 112 is controlled, resulting in a constant cell dispensing rate from the chamber 110 based on the uniform distribution of particulate matter within the volume of fluid sample within the middle region 116, which remains constant to balanced sedimentation in the upper and lower portions of the chamber 110.

Figure 3:
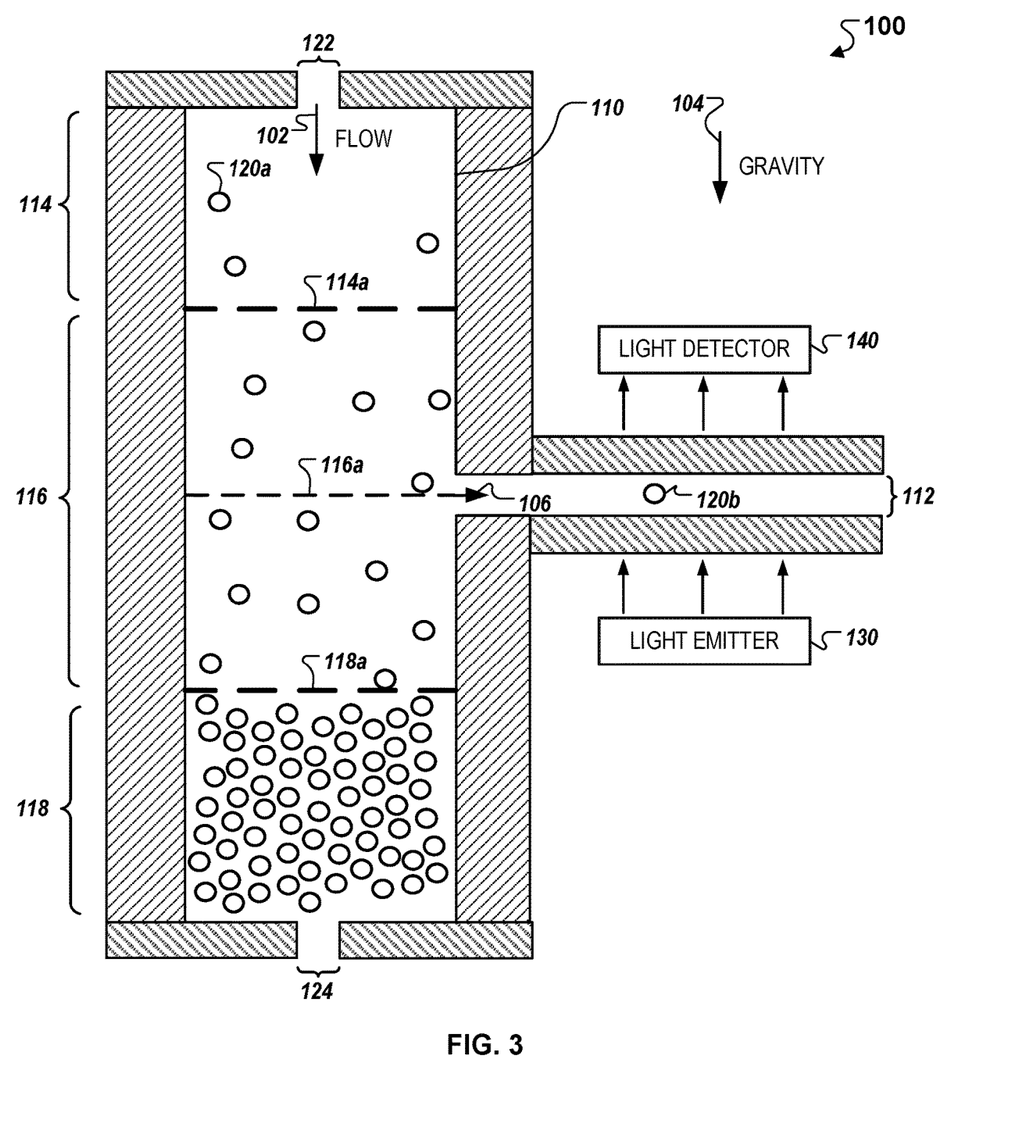
FIG. 3 illustrates a cross-section view of fluid displacement within an exemplary fluid holding and dispensing micro-feature.

FIG. 3 depicts a cross-section view of fluid displacement within an example fluid holding and dispensing micro-feature 100. As shown, the chamber 110 may receive a fluid sample that includes individual particles 120a, and portions of the fluid sample that include particles 120b that are dispensed through the outlet port 112.

The fluid sample can be displaced through the chamber 110 by injecting another fluid (e.g., a reagent fluid, inert fluid) into the chamber 110, which imposes a compression force on the fluid sample that pushes the volume of the fluid sample through the various regions of the chamber 110. In some instances, such another fluid can be injected through an inlet port 122 connected to a portion of the chamber 110 that corresponds to the top region 114, which then displaces the volume of fluid sample inside the chamber 110 from the top region 114 towards the bottom region 118. In such instances, the other fluid can have a lower density of particulate matter relative to the fluid sample.

Additionally and/or alternatively, such another fluid can be injected through a different inlet port 124 connected to a portion of the chamber 110 that corresponds to the bottom region 118, which then displaces the volume of the fluid sample inside the chamber 110 from the bottom region 118 towards the top region 118. In such instances, the reagent fluid has a greater density of particulate matter relative to the fluid sample.

Such another fluid can be injected into the chamber 110 using a fluid actuating device to provide a constant compression force on the fluid sample within the chamber 110. For instance, the actuating device can be configured to inject the other fluid (e.g., reagent fluid) at a particular compression force that ensures that the bulk volumetric flow rate of the fluid sample into the chamber 110 is equal to the bulk volumetric flow rate through an interface 114a between the top region 114 and the middle region 116 to establish steady state conditions as described in FIG. 2. In some implementations, such a fluid actuating device can be located within the analyzer device 30.

In some implementations, the fluid holding and dispensing micro-feature 100 can include multiple inlet ports 122, 124, and/or other inlet ports (not depicted) that are connected to the chamber 110 to support various alternative configurations to inject the fluid sample and the other fluids (e.g., reagent fluids). For example, the fluid sample and the reagent fluid can be injected into the chamber 110 through separate inlet ports 122 and another inlet port (not depicted) that are connected to a portion of the chamber 110 that corresponds to the top region 114. In another example, the fluid sample and the reagent fluid can be injected into the chamber 110 through separate inlet ports 124 and another inlet port (not depicted) that are connected to a portion of the chamber 110 that corresponds to the bottom region 118. In other examples, the fluid sample can be injected through a first inlet port 122 that is connected to a portion of the chamber 110 that corresponds to the top region 114 whereas the reagent fluid can be injected through a second inlet port 124 that is connected to a portion of the chamber 110 that corresponds to the bottom region 118, and vice versa.

In some implementations, the fluid holding and dispensing micro-feature 100 can include other outlet ports (not depicted) that are connected to the chamber 110 to support various alternative configurations to dispense the fluid sample and the other fluids (e.g., reagent fluids). For example, the fluid sample and the reagent fluid can be dispensed from the chamber 110 through separate outlet ports placed on different vertical sidewalls of the chamber 110 along the plane 116a such that the dispensed sample fluid flow through the multiple outlet ports 112 has a normal vector substantially perpendicular to gravity. In other examples, the multiple outlet ports 112 can be placed on different planes of the chamber 110 such that sample fluid and the reagent fluid can be dispensed from different regions of the chamber 110 over different periods of time.

As discussed in FIG. 2, as the fluid sample is displaced through the chamber 110, fractions of the fluid sample develop due to the sedimentation of particulate matter within the fluid sample by the gravitational force 104. This causes the fragmentation of the fluid sample into the top region 114, the middle region 116, and the bottom region 118. As shown, the regions 114-118 are segmented by interfaces 114a and 118a. The volume of fluid sample within the top region 114 includes a low concentration of particles 120a due to the gravitational force 104 causing the particles 120a to sediment downstream towards the bottom region 118. The middle region 116 includes a volume of fluid sample that has a homogenous concentration of the particles 120a. For example, the volume of fluid sample within the middle region 116 may have a uniform cell distribution such that the particles 120a. The bottom region 118 includes a packed layer that has the greatest concentration of particulate matter within the chamber 110. For instance, in examples where the fluid sample is whole blood, sedimentation can cause the top region 114 to contain a plasma supernatant of the whole blood, the middle region 116 to contain pristine blood with concentrations of blood cells that are the same or similar as concentrations when the whole blood was first received in the chamber 110, and the bottom region 118 can contain a packed cell layer with the greatest concentration of cells.

The outlet port 112 is positioned along a portion of the chamber 110 that corresponds to the middle region 116 to ensure that fluid that is dispensed from the chamber 110 has a constant state, which can allow for tests performed using the dispensed fluid to be more accurate and consistent than if fluid were dispensed from either the top region 114 or the bottom region 118. This arrangement of the chamber 110 and the outlet port 112 allows for controlled cell dispensing through the outlet port 112, which is can then be subsequently used to calculate the particulate concentration of the fluid sample within the chamber 110 based on the design principles described in FIG. 2. For instance, since the outlet port 112 is substantially perpendicular to the gravitational force 104, gravity-induced sedimentation within the chamber 110 does not impact the transport of dispensed fluid sample and individual particles 120b through the outlet port 112.

As shown in FIG. 3, as the fluid sample is displaced through the chamber 110 according to a bulk flow 102 that is parallel to gravity, the particles 120a within fluid can be displaced from the top region 114 downstream to the bottom region 118 by the bulk flow 102. As time elapses, three phases of the fluid sample, represented by regions 114-118, generate within chamber 110 due to particulate sedimentation.

Under steady state conditions, as described in FIG. 2, the bulk volumetric flow rate and the particle transport rate of the portion of the fluid sample within the chamber 110 that is dispensed through the outlet port 112 are used to determine the particulate concentration of the fluid sample within the chamber 110. The portion of the fluid sample that is dispensed through the outlet port 112 can be analyzed using the analyzer device 30 as described in FIG. 1. For example, in some instances, the analyzer device 30 can be used to measure a bulk volumetric flow rate and a particle transport rate (or a cell dispense rate), represented by the volume of fluid sample and the number of particles, respectively, that is dispensed through the outlet port 112 over a particular period of time. The analyzer device 30 may use various detection techniques to determine the presence of individual particles 120b within the outlet port 112. For example, in some implementations, as shown in the example in FIG. 3, the analyzer device 30 may use optical techniques to detect light scattering events that indicate the presence of particles 120b within the outlet port 112. In such implementations, the analyzer device 30 may include a light emitter 130 that illuminates a channel connected to the outlet port 112 such that as the particles 120b pass through the channel, a light detector 140 that collects a detection signal based on the number of scattering events over a particular period of time. In other implementations, alternative detection techniques can be used to detect the presence of the particles 120b through the outlet port 112.

The analyzer device 30 can be used to calculate the particulate concentration of the fluid sample that is dispensed through the outlet port 112, for example, based on the expression shown in equation 3:

$$\dot{n}_{outlet} = C_{cell} \times \dot{V}_{outlet} \qquad (3)$$

where $\dot{n}_{outlet}$ represents the particle transport rate (or cell dispense rate) of the portion of the fluid sample that is dispensed through the outlet port 112, $C_{cell}$ represents the particulate concentration of the portion of the fluid sample that is dispensed through the outlet port 112, and $\dot{V}_{outlet}$ represents the volumetric flow rate of the portion of the fluid sample that is dispensed through the chamber 110. As shown in equation 3, the cell dispense rate through the outlet port 112 is equal to the product of the particulate concentration of the fluid sample dispensed through the outlet port 112 and the bulk volumetric flow rate of the flow 106. Using this expression, the measured cell dispense rate, determined by the number of individual cells dispensed through the outlet port 112 over a particular period of time, and the measured volumetric flow rate, determined by the volume of fluid sample that is dispensed through the outlet port 112 over the particular period of time, can be used to calculate the cell concentration of the dispensed portion of the fluid sample.

In some implementations, the fluid sample that is received by the chamber 110 can be whole blood. In such implementations, the fluid holding and dispensing micro-feature 100 can be used, for example, to calculate cell concentrations of analytes within whole blood such as, for example, red blood cells, white blood cells and platelet cells, without substantial pre-processing steps to homogenize whole blood. For example, whole blood can be injected into the fluidic circuit of the cartridge 10, which includes the fluid holding and dispensing micro-feature 100. More specific details related to use of whole blood within the fluid holding and dispensing micro-feature 100 is discussed in FIGS. 5-7.

The micro-feature 100 that is described with regard to and depicted in FIGS. 2-3 can be implemented in a cartridge, such as the example cartridge 10 (e.g., disposable cartridge, reusable cartridge), that is used and controlled by another device, such as the analyzer device 30, to perform various tests on the fluid contained and dispensed by the micro-feature 100. In other implementations, the micro-feature 100 can be incorporated into devices that are performing one or more portions of the analyzing techniques. For example, the micro-feature 100 can be incorporated into the analyzer device 30. Other implementations of the micro-feature 100 are also possible.

Figure 4:
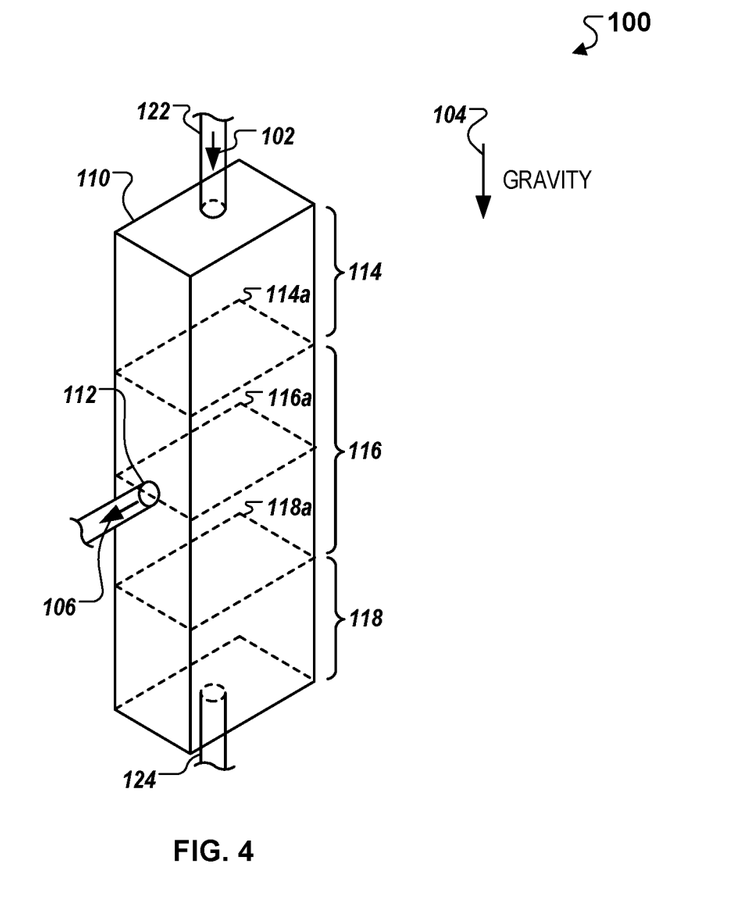
FIG. 4 illustrates a perspective view of an exemplary fluid holding and dispensing micro-feature.

FIG. 4 illustrates a perspective view of an example fluid holding and dispensing micro-feature 100. As shown, the chamber 110 can be enclosed with four vertical sidewalls that form a rectangular chamber 110 along the longitudinal axis of the cartridge 10. In other implementations, other three-dimensional shapes which are of substantially constant cross section, such as, triangular prism and/or cylindrical shapes, can be used as long as the opening of the outlet port 112 that meets the chamber 110 has a normal vector substantially perpendicular to gravity when the micro-feature 100 is positioned to be dispense fluid from within the chamber 110 (e.g., when the cartridge 10 is inserted into the analyzer device 30).

Figure 5:
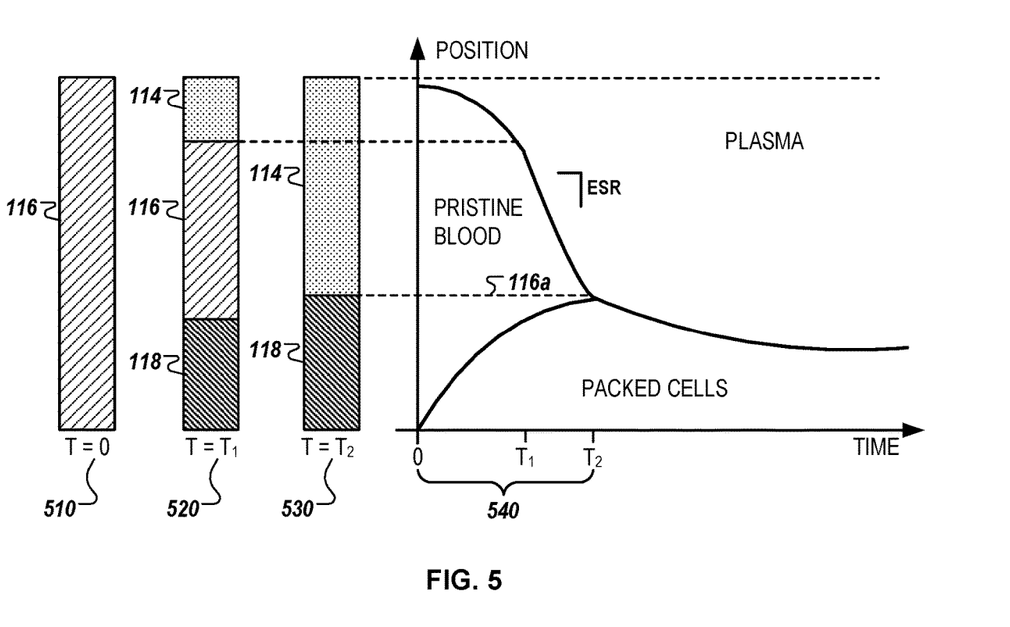
FIG. 5 is a phase diagram representing the spatial content of a sedimenting body of whole blood.

FIG. 5 is a diagram representing the spatial content of an example sedimenting body of whole blood during various time points after injection into the chamber 110. For instance, the diagram 500 represents the vertical position of fractions of whole blood within the chamber 110 as a function of time after the whole blood has been inserted into the chamber 110. As shown, at time point 510, "T=0," the chamber 110 contains only pristine blood, which represents an initial homogenous state of whole blood prior to sedimentation of particulate matter. As time elapses, for example, at time point 520, "T=$T_1$," particulate matter of the whole blood begins to sediment, generating three phases within the microfluidic channel—a cell-deplete plasma supernatant layer that eventually occupies the top region 114, a packed cell layer that eventually occupies the bottom region 118, and a sustained region of pristine blood that separate the plasma supernatant and the packed cell layer within the middle region 114. The vertical height of the pristine blood layer within the chamber 110 reduces as particulate matter within whole blood sediments until at the time point 530, "T=$T_2$," when the supernatant layer collides with the packed cell layer.

The time period between time points 510 and 530, shown as time period 540, represents the total period for which pristine blood layer occupies the middle region 116 of the chamber 110 after inserting whole blood. The duration of the time period 540 can be impacted by the Erythrocyte Sedimentation Rate (ESR), which reflects the rate of sedimentation of whole blood within one hour. In some example implementations, the time period 540 can be between five minutes to three hours depending on the length of the chamber 110.

To ensure that the bulk volumetric flow rate of particles flowing through the outlet port accurately represent the concentration of the particulate matter within whole blood, fluid can be limited to being dispensed by, for example, the micro-feature 100 from within the time period 540 so that only particles from pristine blood layer are analyzed. This ensures that flow through the outlet port 112 results from homogenized fluid with a uniform particulate concentration from the middle region 116 of the chamber 110. As discussed, the fluid holding and dispensing micro-feature 100 provides a technique to inferentially calculate particulate concentration without requiring substantial pre-processing of whole blood, such as centrifugation, dilution, or other techniques that are commonly used in cell counting.

The micro-feature 100 can be configured so that the outlet port 112 is positioned longitudinally along a sidewall of chamber 110 to correspond to the plane 116a that corresponds to the position at which the top region 114 will meet the bottom region 118 at time point 530 (when "T=$T_2$"). For example, the outlet port 112 can extend from one or more sidewalls of the chamber 110 at a vertical position that corresponds to the plane 116a at which the top region 114 and the bottom region 118 meet at time point 530. By positioning the outlet port 112 at this location (corresponding to plane 116a), the micro-feature 110 can maximize a volume of homogenous fluid that can be dispensed by the micro-feature before sedimentation reduces the fluid to only the top and bottom regions 114 and 118, respectively. The plane 116a, and the corresponding position for the outlet port 112, can be different for different types of fluids and/or different types of particulate matter. The plane 116a and the corresponding position for the outlet port 112 can be determined using any of a variety of appropriate techniques for different types of fluids and/or particulate matter, such as through known rates of segmentation for different types of fluids (e.g., the erythrocyte sedimentation rate for whole blood), empirical evidence from testing under use conditions (e.g., sedimentation rate when within the micro-feature 100), and/or other appropriate techniques. In instances in which empirical evidence is used, any of a variety of different statistical operations can be performed on the empirical evidence to determine the plane 116a and the corresponding position for the outlet port 112, such as average values, median values, and/or other appropriate values.

The analyzer device 30 can be configured to determine the time point 530 at which fluid should stop being dispensed from the chamber 110 and through the outlet port 112. The analyzer device 30 can make such a determination based on any of a variety of appropriate techniques. For example, the analyzer device 30 can determine when the time point 530 has been reached for a particular fluid sample that is located in the cartridge 10 based on the calculated particulate concentration of the whole blood that is dispensed through the outlet port 112. For instance, because the cell dispense rate is dependent on particulate concentration, as shown by equation 3, the measured particulate concentration can be compared to a threshold particulate concentration is associated with the packed cell layer of whole blood. In such instances, in response to calculating a particulate concentration of whole blood that is dispensed through the outlet port 112 that is higher than the threshold particulate concentration, the analyzer device 30 may stop dispensing the whole blood from the chamber 110.

In another example, the analyzer device 30 can determine when the time point 530 has been reached and the fluid sample should stop being dispensed from the cartridge 10 based on an amount of time that has elapsed since the fluid was injected into the chamber 110 and a threshold amount of time, for the particular fluid and the particular micro-feature 100, that corresponds to the time period 530. For example, the analyzer device 30 may have predetermined values for the time period 530 that are specific to various fluids, particulate matter, and/or micro-feature 100 configurations. The analyzer device 30 can identify when a corresponding time period 530 has been met based on an amount of time that has elapsed since the fluid was injected into the chamber 110 of the cartridge 10. The amount of time that has elapsed can include an amount of time since the cartridge 10 was inserted (or otherwise made accessible to) the analyzer device 30, and an amount of time between when the fluid was be injected into the cartridge 10 and when the cartridge 10 was inserted into the analyzer device 10. The latter time period (time between injection of fluid and insertion into analyzer device 30), can be timed by the analyzer device 30 (e.g., medical professional can provide input (e.g., button press, verbal input) indicating when injection is occurring) and/or estimated by the analyzer device 30 (e.g., average time for medical professional to perform injection and insertion steps).

Figure 6:
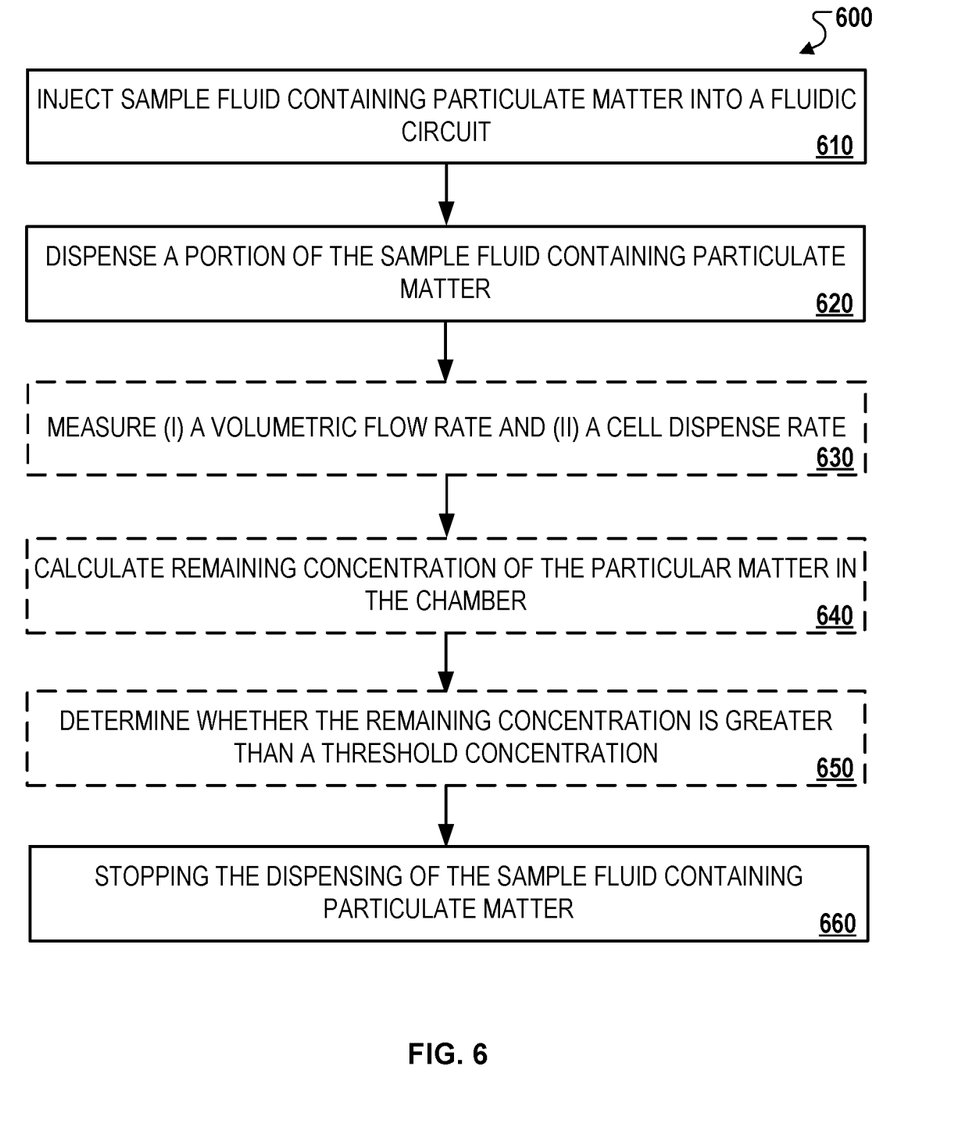
FIG. 6 illustrates an exemplary process for holding and dispensing fluid.

FIG. 6 is a flowchart of an example technique 600 for holding and dispensing fluid. Briefly, the example technique 600 includes injecting fluid containing particulate matter into a fluidic circuit (610), dispensing a portion of the fluid containing particulate matter (620), and stopping the dispensing of the fluid containing particulate matter (660). In some implementations, the technique 600 may optionally include measuring (i) a volumetric flow rate, and (ii) a cell dispense rate (630), calculating a remaining concentration of the particulate matter in the chamber (640), and determining whether the remaining concentration is greater than a threshold concentration (650).

In more detail, the technique 600 includes injecting fluid containing particulate matter into a fluidic circuit (610). For example, whole blood can be injected into the fluidic circuit of the cartridge 10, which includes the chamber 110 that has one or more surfaces that define a volume to receive the whole blood. As described previously in FIGS. 3 and 5, after a certain time period from when the whole blood enters the chamber 110, the chamber 110 may include a top region 114 that contains plasma supernatant, a middle region 116 that contains pristine blood, and a bottom region 118 that contains packed cells due to sedimentation.

The technique 600 also includes dispensing a portion of the fluid containing particulate matter (620). For example, a portion of the whole blood that contains pristine blood can be dispensed from the middle region 116 into the outlet port such that the flow of the dispensed whole blood is substantially perpendicular to gravity. As described in FIG. 3, the pristine blood that is dispensed from the middle region 116 contains a homogenous concentration of red blood cells, which results in a constant particle transport rate of cells that are dispensed through the outlet port 112.

In some implementations, the technique 600 can also include measuring (i) a volumetric flow rate, and (ii) a cell dispense rate (630). For example, the analyzer device 30 can be used to determine a volumetric flow rate corresponding to the volume of whole blood that is dispensed through the outlet port 112 over a period of time after the whole blood is received by the chamber 110.

The analyzer device 30 may also be used to determine a cell dispense rate corresponding the number of individual red blood cells that are dispensed through the outlet port 112. For instance, as described in FIG. 3, in some implementations, the analyzer device 30 may include the light emitter 130, which illuminates the pathway connected through the outlet port 112, and the light detector 140, which detects a number of scatter events over a particular period of time after the whole blood is received by the chamber 110. In such instances, the light emitted by the light emitter 130 can be scattered by individual red blood cells, and the light detector may determine the number of red blood cells passing dispensed through the outlet port based on the number of scattering events.

In some implementations, the technique 600 can also include calculating a remaining concentration of the particulate matter (640). For example, the analyzer device 30 can calculate a remaining concentration of red blood cells within the chamber 110 based on the measured volumetric flow rate and the cell dispense rate through the outlet port 112. As discussed in FIG. 3, under steady state conditions, the cell dispense rate through the outlet port 112 can be related to the red blood cell concentration and the volume of whole blood ejected from chamber 110 using equation 3.

In some implementations, the technique 600 can also include determining whether the remaining concentration is greater than a threshold concentration (650). For example, the analyzer device 30 can be used to determine whether the remaining concentration of red blood cells of the whole blood that is being dispensed through the outlet port 112 greater than a threshold concentration. For instance, the threshold concentration can be the concentration of red blood cells in the packed cell layer of whole blood contained in the bottom region 118 of the chamber 110.

In some implementations, after determining that the red blood cell concentration of the whole blood being dispensed through the outlet port 112 exceeds the threshold concentration, the analyzer 30 can stop the dispensing based on determining that pristine blood is no longer being dispensed through the outlet port 112. As discussed in FIG. 5, the time point associated with when the red blood cell concentration of the whole blood exceeds the threshold concentration corresponds to the time point 530.

The process 600 can include stopping the dispensing of the fluid containing particulate matter (660). For example, dispensing of the whole blood through the outlet port 112 can be stopped after a specified time period when the chamber 110 contains only plasma supernatant or packed cells. As described previously in FIG. 5, after the time period 540, the whole blood within the chamber 110 only contains plasma supernatant and a packed cell layer. After this time period, dispensing can be stopped because the whole blood within the chamber 110 may not have a uniform distribution of red blood cells, which may cause errors in concentration calculations described by equation 3.

In some implementations, dispensing can be stopped in response to determining that pristine blood is no longer being dispensed through the outlet port 112. For instance, the analyzer device 30 may initially calculate the red blood cell concentration of the whole blood being dispensed through the outlet port 112 and then compare the calculated red blood cell concentration to a threshold concentration associated with the red blood cell concentration of the packed cell layer of the whole blood. If the calculated red blood cell concentration exceeds the threshold concentration, then the analyzer device 30 may determine that only whole blood that includes the packed cell layer is being dispensed through the outlet port 112.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method comprising:
   providing a fluidic circuit comprising at least:
   (i) a chamber having one or more surfaces that define a volume to receive fluids containing particulate matter, and
   (ii) an outlet port located in a middle region of the chamber; injecting a first fluid containing particulate matter into the chamber of the fluidic circuit;
   determining that a first threshold time period has elapsed after injecting the first fluid into the chamber of the fluidic circuit, wherein once the first threshold time period is determined to have elapsed, the first fluid injected into the chamber of the fluidic circuit comprises a top region, a middle region, and a bottom region that each contain different concentrations of the particulate matter due to sedimentation of the particulate matter in the chamber;

based on determining that the first threshold time period has elapsed, dispensing, via the outlet port, a volume of the middle region of the first fluid such that the dispensing volume of the middle region of the first fluid flows from the chamber and into the outlet port in a direction that is perpendicular to a longitudinal axis of the chamber:

determining that a second threshold time period has elapsed after injecting the first fluid into the chamber of the fluidic circuit, wherein once the second threshold time period is determined to have elapsed, the top region and bottom region of the first fluid include a remaining volume of the first fluid that does not include the volume of the middle region of the first fluid: and based on determining that the second threshold time period has elapsed, stopping the dispensing of the volume of the middle region of the first fluid while the top region and bottom region of the first fluid still include the remaining volume of the first fluid.

2. The method of claim 1, further comprising:

measuring, by an analyzer device, particle concentration in the volume of the middle region of the first fluid that flows through the outlet port over a particular period of time;

measuring, by the analyzer device, a total volume of the first fluid dispensed through the outlet port over the particular period of time;

after the dispensing, calculating, by the analyzer device, a remaining concentration of the particulate matter in the first fluid in the top region, the middle region, and the bottom region of the first fluid based at least on (i) the number of individual particles measured as flowing through the outlet port, and (ii) the measured total volume of the first fluid dispensed over the period of time; and determining, by the analyzer device, if the remaining concentration of the particulate matter in the first fluid in the top region, the middle region, bottom region of the first fluid is greater than a threshold concentration for dispensing through the outlet port, wherein the remaining concentration of the particulate matter is greater than the threshold concentration for dispensing the outlet port.

3. The method of claim 2, wherein:

the first fluid containing particulate matter injected into the chamber of the fluidic circuit is whole blood, and calculating, by the analyzer device, the remaining concentration of the particulate matter comprises determining red blood cell concentration of whole blood in the top region, the middle region, and the top region of the first fluid.

4. The method of claim 2, wherein prior to dispensing, the middle region of the first fluid has a threshold concentration of the particulate matter that is (i) greater than a first threshold concentration of the particulate matter within the first fluid chamber, and (ii) less than a second threshold concentration of the particulate matter within the bottom region of the first fluid.

5. The method of claim 2, wherein the analyzer device comprises one or more optical detectors.

6. The method of 1, wherein dispensing the volume of the middle region of the first fluid comprises:

injecting a second fluid into the chamber after injecting the first fluid containing particulate matter into the fluidic circuit, wherein the second fluid forces individual particles from among the particulate matter of the first fluid to be dispensed through the outlet port.

7. The method of claim 6, wherein:

injecting the second fluid into the chamber comprises injecting the second fluid into at least one of one or more inlet ports that is connected to the chamber, the second fluid is less dense than the first fluid containing particulate matter and the one or more inlet ports are different from the outlet port.

8. The method of claim 6, wherein injecting the second fluid into the chamber comprises injecting the second fluid into at least one of one or more inlet ports that is at and connected to a bottom region of the chamber;

the second fluid is more dense than the first fluid containing particulate matter; and the one or more inlet ports are different from the outlet port.

9. The method of claim 1, wherein:

the first fluid containing particulate matter injected into the chamber of the fluidic circuit is whole blood; and after the first threshold time period is determined to have elapsed, the top region contains a plasma supernatant of the whole blood, the middle region of the first fluid contains a portion of the whole blood with blood cell concentrations that are within a threshold range of a blood cell concentration of the whole blood when it is initially received into the chamber, and the bottom region of the first fluid contains a cell layer that results from sedimentation during the first threshold time period.

10. The method of claim 1, further comprising:

dispensing, via a second outlet port of the chamber, a volume of the middle region of the first fluid such that the dispensed volume of the middle region of the first fluid flows from the chamber and into the second outlet port in a direction that is perpendicular to the longitudinal axis of the chamber.

11. The method of claim 1, wherein:

the chamber has a circumference that extends throughout the longitudinal axis of the chamber; and the chamber provides unimpeded fluidic communication along the longitudinal axis of the chamber within the entire circumference of the chamber.

* * * * *

UNITED STATES PATENT AND TRADEMARK OFFICE
CERTIFICATE OF CORRECTION

PATENT NO. : 10,612,070 B2
APPLICATION NO. : 15/397349
DATED : April 7, 2020
INVENTOR(S) : McPeak et al.

Page 1 of 1

It is certified that error appears in the above-identified patent and that said Letters Patent is hereby corrected as shown below:

On the Title Page

Item (57), (Abstract), Line 11, delete "them," and insert -- time, --, therefor.

In the Claims

Column 16, Line 60-61, in Claim 1, after "surfaces" delete "that define a volume".

Column 17, Line 14, in Claim 1, delete "chamber:" and insert -- chamber; --, therefor.

Column 17, Line 21, in Claim 1, delete "fluid:" and insert -- fluid; --, therefor.

Column 18, Line 3, in Claim 4, before "first" insert -- top region of the --.

Column 18, Line 3, in Claim 4, delete "fluid chamber," and insert -- fluid, --, therefor.

Column 18, Line 8, in Claim 6, after "of" insert -- claim --.

Column 18, Line 19, in Claim 7, delete "chamber," and insert -- chamber; --, therefor.

Column 18, Line 33, in Claim 7, delete "matter" and insert -- matter; --, therefor.

Column 18, Line 24, in Claim 8, delete "wherein" and insert -- wherein: --, therefor.

Signed and Sealed this
Ninth Day of June, 2020

Andrei Iancu
*Director of the United States Patent and Trademark Office*